United States Patent [19]

Ma et al.

[11] Patent Number: 5,236,570
[45] Date of Patent: Aug. 17, 1993

[54] HEPARIN-SELECTIVE POLYMERIC MEMBRANE ELECTRODE

[75] Inventors: Shu-Ching Ma; Mark E. Meyerhoff; Victor C. Yang, all of Ann Arbor, Mich.

[73] Assignee: University of Michigan, Ann Arbor, Mich.

[21] Appl. No.: 849,218

[22] Filed: Mar. 10, 1992

[51] Int. Cl.$^5$ .......................................... G01N 27/26
[52] U.S. Cl. ................................... 204/418; 204/403; 204/416; 435/817
[58] Field of Search .............. 204/403, 415, 416, 418, 204/153.12; 435/817

[56] References Cited

U.S. PATENT DOCUMENTS

| | | | |
|---|---|---|---|
| 4,214,968 | 7/1980 | Battaglia et al. | 204/418 |
| 4,440,218 | 4/1984 | Wilkins | 128/635 |
| 4,810,351 | 3/1989 | Chapoteau et al. | 204/153.16 |
| 4,861,455 | 8/1991 | Sugihara et al. | 204/418 |

OTHER PUBLICATIONS

Grode, et al., *J. Biomed. Mater. Res. Symposium*, No. 3, pp. 77–82 (1972).
Hartman, et al., *Mikrochimica Acta* [Wein], 1978 II 235–246.
Wegmann, et al., *Mikrochimica Acta* [Wein], 1984 III 1–16.

*Primary Examiner*—John Niebling
*Assistant Examiner*—Bruce F. Bell
*Attorney, Agent, or Firm*—Rohm & Monsanto

[57] ABSTRACT

An anion exchange membrane for ionic macromolecules, specifically heparin, which is formed of a polymeric matrix material, an anion exchange material suitable for heparin detection, and a plasticizer can be employed in an electrochemical sensor arrangement to directly measure the concentration of heparin ions in blood or blood fluid. Potentiometric response to heparin has been observed with membranes comprising 30–70 wt. % polymeric matrix material, such as polyvinyl chloride, 0.1–12 wt. % quaternary ammonium salt, such as tridodecyl methyl ammonium chloride, and 30–70 wt. % of a plasticizer, such as dioctyl sebacate.

19 Claims, 3 Drawing Sheets

HEPARIN-SELECTIVE POLYMERIC MEMBRANE ELECTRODE

STATEMENT OF GOVERNMENT RIGHTS

This invention was made with government support under Grant No. R29-HL38353 awarded by the National Institutes of Health. The government has certain rights in the invention.

BACKGROUND OF THE INVENTION

This invention relates generally to a polymer membrane type ion-selective electrode, and more particularly, to a polymer membrane type ion-selective electrode suitable for monitoring polyionic macromolecules such as heparin.

Polymer membrane type ion-selective electrodes are now routinely used in commercial biomedical instruments to measure accurately levels of clinical important small ions, such as $Ca^{++}$, $Na^+$, $K^+$, $Li^+$, $H^+$, and $Cl^-$, in undiluted whole blood. These ion-selective electrodes typically comprise a highly plasticized polymeric matrix material with an ion-exchange material or ion-complexing agent therein. The ion-exchange material may be a quaternary ammonium salt, such as tri-dodecyl methyl ammonium chloride (TDMAC).

Polyvinyl chloride (PVC) is a common polymeric membrane matrix material used in the art of solid-state or liquid-membrane electrodes for the detection of small ions (see, for example, U.S. Pat. No. 4,861,455 or Hartman, et al., "Chloride-Selective Liquid-Membrane Electrodes Based on Lipophilic Methyl-Tri-N-Alkyl-Ammonium Compounds and Their Applicability to Blood Serum Measurements," *Mikrochimica Acta* [Wein], 1978 II 235-246).

Efforts to develop similar sensors, including immuno-based biosensors, for the detection of large biomolecules, such as proteins or drugs, have thus far been unsuccessful. One of the most difficult problems has been identifying appropriate complexing agents and membrane chemistries that yield significant, specific and reversible electrochemical responses to the desired analyte. Even if a specific complexing agent is identified for a macromolecular biomolecule, whether the interaction with the macromolecular ion is strong enough to overcome the rather low mobility of a large ion to yield to significant electrochemical response remains in question. In theory, the sensitivity and selectivity of an ion-selective electrode membranes is governed by both the mobility of the analyte ion and the strength of the interaction between the ion-complexing agent and the analyte ion. In addition, strong interference resulting from a high concentration of small ions, such as chloride ions, in a blood sample may dictate the membrane's response.

An analyte of particular clinical significance is heparin, a polyanionic macromolecule. Heparin is the anti-coagulant drug used universally in surgical procedures and extracorporeal therapies, and for the prevention of thromboembolism following surgery or childbirth. Heparin is a group of polydisperse (molecular weight ranges from 5,000 to 30,000 daltons) straight-chain anionic mucopolysaccharides called glycosaminoglycans having an average molecular weight of 15,000 daltons. Glycosaminoglycans are copolymers of sulfated ($SO_3^-$) and unsulfated uronic/iduronic acids alternating with glucosamine residues.

The major side effect of heparin administration is bleeding. In fact, a survey by the Boston Collaborative Drug Surveillance Program on drug-related deaths among in-patients indicted that heparin is the drug responsible for a majority of drug deaths in reasonably healthy patients. In view of this morbid potential, there is a great need for a means to continuously and accurately measure heparin levels in the bloodstream during surgical procedures. Unfortunately, there currently is no method suitable for direct and rapid determination of the physiological heparin levels. Presently available heparin assays, such as the Activated Clotting Time, are all based on blood clotting time. Further, the prior art assays are not specific to heparin and lack speed, accuracy, consistency, and a defined biochemistry. Further, since the clotting time based heparin assays can not directly measure the blood heparin level, the role of heparin in the associated bleeding complications and the mechanism of the "heparin rebound" phenomenon have never been identified. There is, therefore, a need for a means of directly measuring the levels of heparin in the blood in both clinical practice and medical research.

The quaternary ammonium salt TDMAC is known to bind or complex with heparin. In fact, it is well-known in the medical arts to fabricate thromboresistant biomaterials by heparinizing the surface of a TDMAC-coated or impregnated polymer. TDMAC shares significant structural similarity to polybrene, a synthetic polyquarternary ammonium salt, considered to be one of the most potent heparin antagonists. Although TDMAC has been used as the anion-exchange material in conventional membrane electrodes for the detection of small ions, the art is totally devoid of any suggestion that macromolecules, such as heparin, could be directly detected with TDMAC-doped PVC membranes.

It is, therefore, an object of this invention to provide an electrochemical sensor for ionic macromolecules.

It is another object of this invention to provide an electrochemical sensor for direct measurement of heparin in whole blood or plasma.

It is also an object of this invention to provide an electrochemical sensor for direct measurement of heparin in whole blood or plasma which is accurate over the expected clinically relevant concentration range.

It is a further object of this invention to provide an electrochemical sensor for direct measurement of heparin in whole blood or plasma which possesses adequate dynamic response characteristics, i.e., responds rapidly to a change in ion concentration and returns promptly to baseline, so that it is suitable for continuous in vivo monitoring.

It is additionally an object of this invention to provide a polymeric membrane electrode having specific selectivity for heparin macromolecules even in the presence of $Cl^-$ and other anionic impurities.

SUMMARY OF THE INVENTION

The foregoing and other objects are achieved by this invention which provides, in one embodiment, an anion exchange membrane for ionic macromolecules, specifically heparin, which is formed of a polymeric matrix material, an anion exchange material suitable for heparin detection, and a plasticizer. The anion exchange material is dispersed or dissolved in the plasticized polymeric matrix material.

PVC has been found to produce potentiometric response to heparin when used as the polymeric matrix material of the anion exchange membrane of the present invention. Although the examples herein are directed to formulations using PVC as the polymeric matrix material, it is to be specifically understood that other film-forming, hydrophilic polymers are suitable matrix materials. Various polymeric materials of the type used in electrode membranes can be used including synthetic and natural polymeric materials such as polymers and copolymers of ethylenically unsaturated monomers such as polyethylenes, poly(1,2-butadienes) and the like; polycondensation polymers, such as polyesters, polyamides, polyurethanes, etc. Such various polymers specifically include, without limitation, polyurethane, cellulose triacetate, and poly(vinyl alcohol)/poly(vinylchloride) copolymer. For body-invasive uses, the polymeric matrix material should be biocompatible.

One or more plasticizers may be used in the membrane composition in order to maintain homogeneity of the mixture. A particularly preferred plasticizer is dioctyl sebacate (DOS). However, other plasticizers are suitable for preparing anion exchange membranes in accordance with the present invention. Such other plasticizers include, without limitation, isopropyl palmitate, isopropyl isostearate, diisooctyl phthalate, and the other plasticizers listed on Table II below. In selecting a plasticizer for the polymeric membrane, it is important that the plasticizer is compatible with the polymeric matrix material. Incompatibility manifests itself, for example, as exudation of the plasticizer during curing.

The anion exchange material is preferably a quaternary ammonium salt. In particularly preferred embodiments of the invention, the quaternary ammonium salts which produced optimum results are TDMAC and aliquat 336 (trioctyl methyl ammonium chloride). Other quaternary ammonium salts which produce a potentiometric response include, without limitation, trimethyl phenyl ammonium chloride, dimethyl dioctadecyl ammonium bromide, tetramethylammonium, polybrene, and the other quaternary ammonium salts list on Table III below. In addition to quaternary ammonium salts, quaternary phosphonium salts or quaternary arsonium salts may be used in the practice of the invention.

Selectivity and sensitivity are affected by the contents of the polymeric membranes. In preferred embodiments, potentiometric response to heparin has been observed with membranes comprising 30-70 wt. % polymeric matrix material; 30-70 wt. % plasticizer; and 0.1-12 wt. % quaternary ammonium salt. Particularly preferred embodiments comprise about 65 wt. % PVC, about 33 wt. % DOS, and 1.4-2.0 wt. % TDMAC.

In certain preferred embodiments, the anion exchange membrane is prepared as a homogenous solution of the polymeric matrix material, plasticizer, and anion exchange material in a suitable organic solvent, such as tetrahydrofuran (THF) or dimethylformamide (DMF), which is suitable for casting into a thin film. The thin film can be cut to size for mounting on an electrode body as will be described hereinbelow. Typically, the membrane thickness is in the range of about 100 $\mu$m to 300 $\mu$m, preferably, ~200 $\mu$m.

In a specific device embodiment, a membrane electrode of the type having an ion-selective membrane constructed in accordance with the principles of the invention comprises:
(a) a housing for containing a reference solution;
(b) an electrode, such as a Ag/AgCl electrode, arranged in the housing so that it is disposed in the reference solution and is connected electrically to a potentiometer and reference electrode, such as a Ag/AgCl double junction reference electrode; and
(b) the heparin-selective membrane of the present invention which is disposed on one end of the housing so as to seal the reference solution inside the housing and to contact a sample solution external to the housing.

In alternative device embodiments, the anion exchange membrane solution may be layered or coated on a conductive metallic substrate or surface, such as a conductive wire.

In a method of use aspect of the present invention, the concentration of heparin in a liquid medium is measured as a function of its potentiometric response using a membrane electrode fabricated in accordance with the principles of the invention. The liquid medium may be a body fluid, such as blood or blood components.

BRIEF DESCRIPTION OF THE DRAWING

Comprehension of the invention is facilitated by reading the following detailed description, in conjunction with the annexed drawing, in which.

DETAILED DESCRIPTION

An understanding of the invention can be enhanced by reference to the following examples of specific embodiments.

EXAMPLE 1

In a particularly preferred specific embodiment, a heparin-selective polymer membrane is prepared which comprises:
1.5 weight percent TDMAC;
65.7 weight percent PVC; and
32.8 weight percent dioctyl sebacate (DOS).

A polymer casting solution is prepared by dissolving 132 mg PVC, 66 mg DOS, and 3-4 mg TDMAC in ~1.5 ml THF solvent. This solution is cast into a glass ring (i.d.=22 mm) on a glass slide. The solvent is permitted to evaporate, illustratively overnight, to form a thin film of ~200 $\mu$m in thickness.

Figure 1:
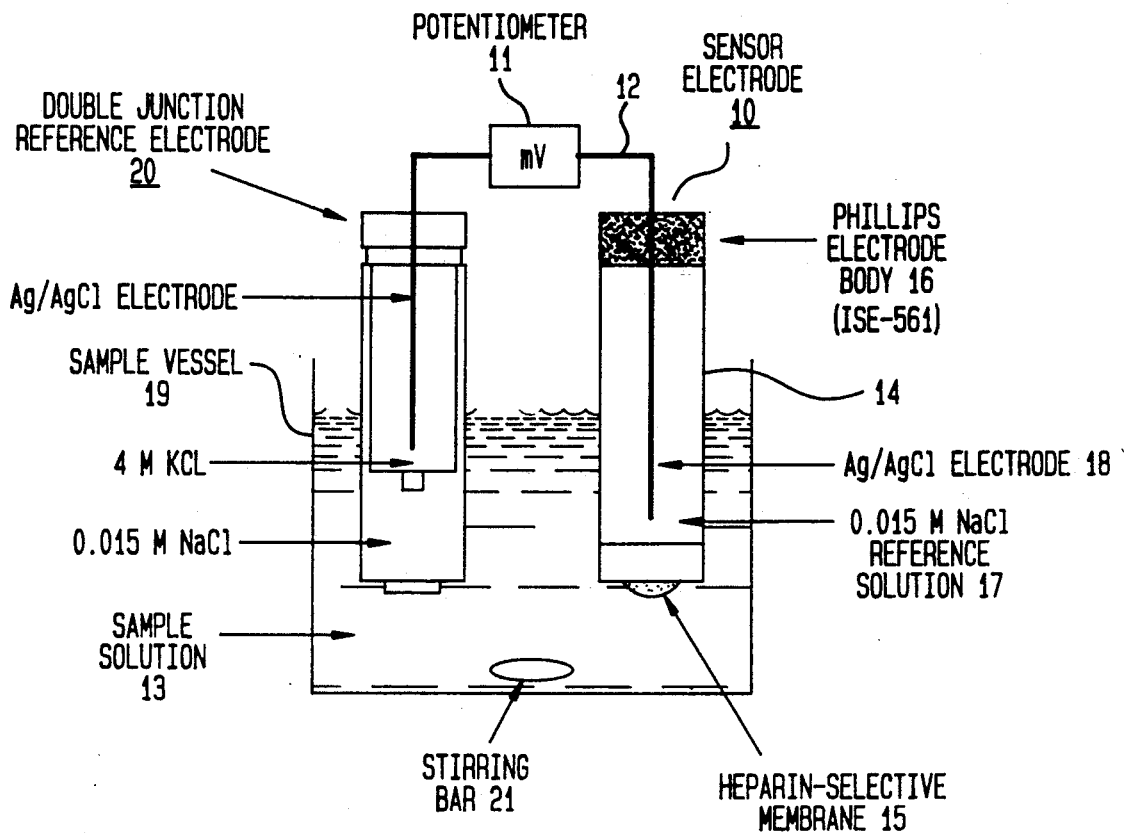
FIG. 1 is a schematic representation of an assembly for the measurement of an analyte solution with a heparin-selective polymeric membrane electrode in accordance with the invention.

FIG. 1 is a schematic representation of an assembly for the measurement of an analyte solution with a heparin-selective polymeric membrane electrode 10. In this embodiment of the invention, a thin heparin-selective polymer membrane 15 constructed in accordance with the principles of the invention is mounted onto the tip of a conventional Philips ISW-561 electrode body 16 (available from Glasblaserei Moller, Zurich, Switzerland). Electrode body 16, includes housing 14 for containing a reference solution 17, in this case 0.015M NaCl, and a Ag/AgCl electrode 18 which is disposed in reference solution 17 and connected electrically by wire 12 to potentiometer 11 and reference electrode 20, in this case a Ag/AgCl double junction reference electrode.

Referring to FIG. 1, a potentiometric response of an analyte in sample solution 13 contained in sample vessel 19 was measured relative to outer Ag/AgCl double junction reference electrode 20 at ambient room temperature ($\sim 22°$ C.). Sample solution 13 was stirred with a magnetic stirring bar 21 during all experiments.

Figure 2:
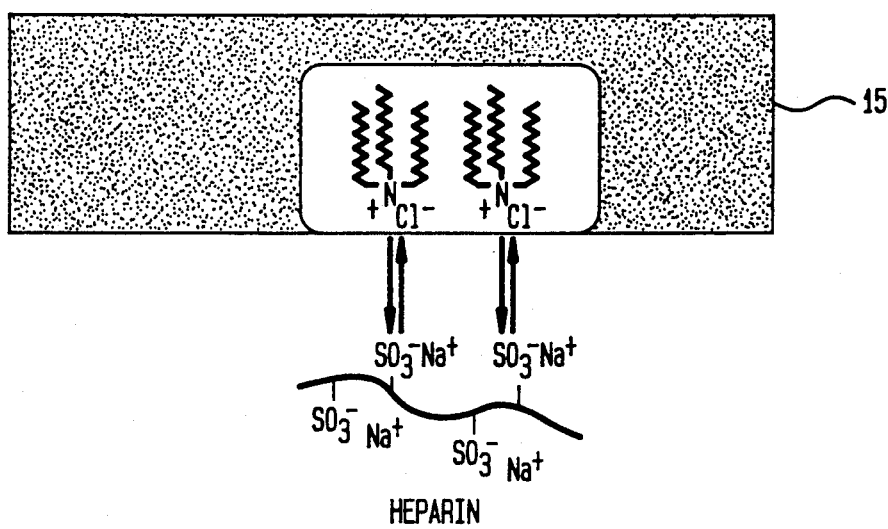
FIG. 2 is a schematic representation of the heparin-selective polymeric membrane and solution interface during operation of the heparin-selective polymeric membrane electrode of FIG. 1.

Heparin-selective polymeric membrane 15 serves as the interface between sample solution 13 and reference solution 17. FIG. 2 is a schematic representation of the heparin-selective polymeric membrane and solution interface during operation of the heparin-selective polymeric membrane electrode of FIG. 1.

Figure 3:
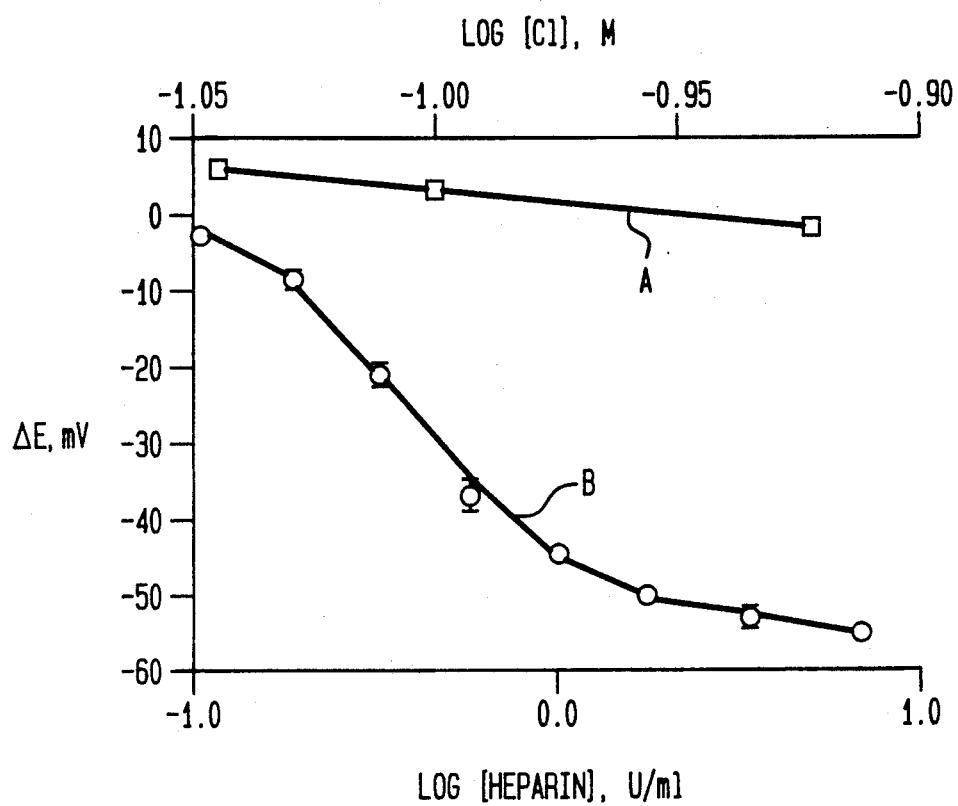
FIG. 3 is a graphical representation of the response characteristics of a heparin-selective electrode to $Cl^-$ ions (Line A) and heparin (Line B) over their respective physiological concentration range. The potential change ($\Delta E$) in mV from the original cell potential is plotted against the logarithm of the concentration of the analytes in clinical activity units per ml (U/ml)

FIG. 3 is a graphical representation of the response characteristics of a heparin-selective electrode (as in Example 1) to Cl$^-$ ions and heparin over their respective physiological concentration range. $\Delta E$ represents the potential change (i.e., the cell potential) in mV relative to the absolute potential reading in 0.12 NaCl (i.e., without added heparin or varying chloride concentration). $\Delta E$ is plotted against the logarithm of the concentration of the analytes in U/ml. The data were obtained in duplicate from two different electrodes and plotted as the mean $\pm$ standard deviation (SD). Referring to FIG. 3, line (A) is the response to solutions of NaCl at concentrations ranging from 0.09 to 0.12M (data points designated as "□") and line (B) is the response to aqueous solutions of heparin and 0.12M NaCl (data points designated as "○").

Despite the presence of a high level of chloride ions (0.12M) in the sample, the heparin-selective electrode of the present invention exhibited sensitivity to very low levels of heparin in the aqueous solution. A linear region, covering the concentration range from 0.2 to 1.0 U/ml heparin, is observable on FIG. 3, Line (B). Membranes formulated with 30–40% by weight plasticizer exhibit selective potentiometric response to the highly sulfated heparin macromolecule relative to chloride over their respective physiological concentration ranges. The electrode detects low levels of heparin (0.2-1.0 U/ml) even in the presence of 0.12M chloride.

No response was observed to heparin when a thin dialysis membrane (molecular weight cutoff=12,000 daltons) was placed over the outer surface of the polymer membrane to block the heparin-TDMAC interaction. Further, the addition of protamine to a heparin sample immediately shifted the potential of the electrode toward a more positive direction. Protamine is a clinically-used heparin antagonist that binds heparin through electrostatic interaction and thereby decreases the activity of free heparin in the solution. These observations indicate that the heparin-selective electrode of the present invention is responding directly to heparin macromolecules and not to small ionic impurities which might be present in the heparin samples.

Figure 4:
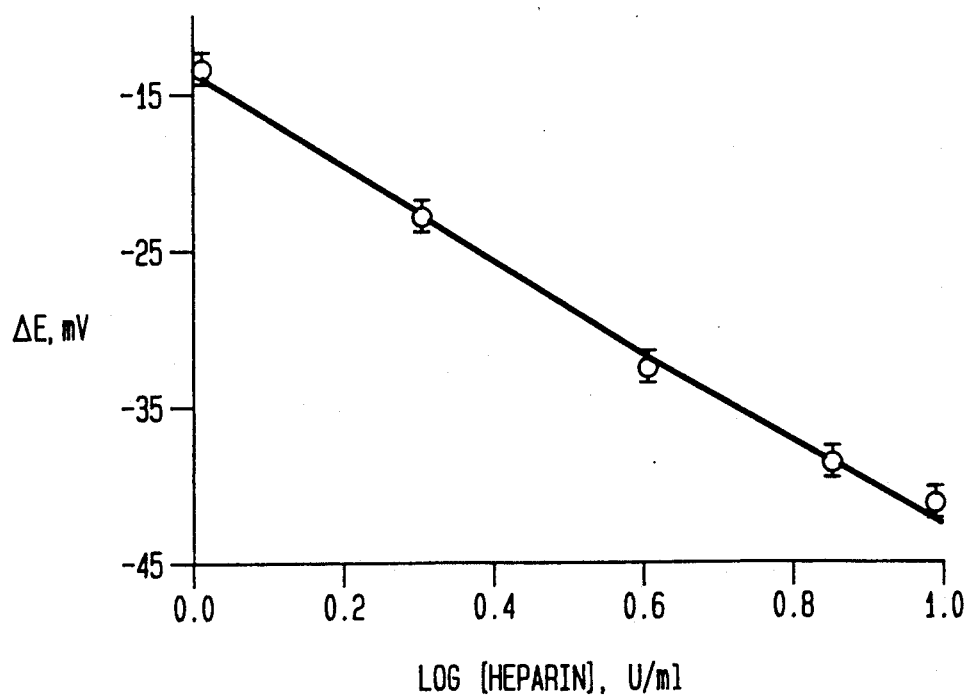
FIG. 4 is a graphical representation of the response characteristics of a heparin-selective electrode to heparin in citrated fresh human plasma samples.

FIG. 4 is a graphical representation of the response characteristics of a heparin-selective electrode to heparin in citrated fresh human plasma samples. The potential change, $\Delta E$, in mV is plotted against the logarithm of the heparin concentration in U/ml. The plot shown in FIG. 4 exhibits a linear relationship ($r^2=0.99$) between the voltage change and the logarithm of heparin concentration over the concentration range tested (1.0 to 9.8 U/ml). The heparin levels encountered in most surgical procedures are within the range of 1.0 to 8.0 U/ml. Thus, the sensitivity of the heparin-selective electrode of the present invention is adequate for clinical purposes.

The response of the heparin-selective electrode to a wide range of related molecular species was measured and the results are shown in Table I. Such related species include the glycosaminoglycan analogs dermantin sulfate (Derm-S), chondroitin sulfate A (Chon-A), and hyaluronic acid (Hya). Other tested species were a highly sulfated anionic polymer, poly(vinylsulfate) (PVS) and sulfated and non-sulfated glucosamine residues (major monosaccharide building blocks of heparin). All tested compounds were prepared in 0.12M NaCl solution at the same concentration (12 $\mu$g/ml). For heparin, 12 $\mu$g/ml is approximately equivalent to 1.2 U/ml clinical activity. Unless otherwise specified, the compounds were in their sodium salt form.

TABLE I

POTENTIOMETRIC RESPONSE OF THE HEPARIN SENSOR TOWARD VARIOUS COMPOUNDS

| Tested Compounds (12 $\mu$g/ml) | $\Delta E$, m.V. | Sulfate Content (wt %) |
|---|---|---|
| Hep | −50 | 13.0 |
| Derm-S | −25 | 9.0 |
| Chon-A | −10 | 7.0 |
| Hya | 0 | 0 |
| PVS | 0 | 62.0 |
| Glucosamine | 0 | 0 |
| Glucosamine 2-sulfate | 0 | 25.0 |
| Glucosamine 3-sulfate (free acid) | 0 | 27.0 |
| Glucosamine 6-sulfate (free base) | 0 | 27.0 |
| Glucosamine 2,3-disulfate | 0 | 42.0 |

Referring to Table I, the potentiometric response to heparin was superior to the response observed to the other species with reducing response to other glycosaminoglycan analogs in direct correlation with the sulfate content of these compounds. However, the electrode displayed no measurable response to PVS despite the fact that PVS contains up to 62 wt. % sulfate. Likewise, none of the glucosamine residues yielded detectable potentiometric signals.

Although not wishing to be bound by any theory, the preferred extraction of heparin to sulfated glucosamine residues may be due to the ability of heparin to interact simultaneously with a large number of immobile positively charged tridodecyl ammonium sites in the hydrophobic membrane (see FIG. 2), whereas the lack of response to PVS may be attributed to the rather hydrophilic nature of PVS that prohibits its extraction by the hydrophobic organic membrane. Previous studies with ion-exchanger based membrane electrodes suggested that the response mechanism involves the extraction of the substrate into the organic membrane phase, and the concomitant ion-pairing of the substrate at the sites of the complexing agent. The equilibrium constant for the ion-exchange extraction appears to dictate the observed electrode selectivity.

EXAMPLE 2

The potentiometric response to heparin for various heparin-selective polymer membrane compositions plasticized with different plasticizers are summarized in Table II below. The compositions of Table II basically comprise 66 mg PVC, ~132 mg plasticizer, and 6 mg Aliquat 336 as the quaternary ammonium salt. The weight percentages of the various components are given in parentheses on the table. The potential response is shown on the table as ΔE (mV) between an aqueous 0.15M NaCl solution and 6.9 U/ml heparin in an aqueous solution of 0.15M NaCl.

Excellent response was achieved with membranes (j) and (k).

TABLE III

POTENTIOMETRIC RESPONSE TO HEPARIN AND COMPOSITIONS OF MEMBRANES COMPOSED OF 66 MG PVC, ~132 MG DOS AND 6 MG QUATERNARY AMMONIUM SALT

| Membrane | ΔE 0–6.9 U/ml (in 0.15M NaCl) | 4° ammonium salt | 66 mg PVC (wt %) | mg of DOS (wt %) | 6 mg of 4° salt (wt %) |
|---|---|---|---|---|---|
| a | −3.6 | Triethyl phenyl ammonium iodide | (32.31) | 132.6 (64.90) | (2.94) |
| b | −4.4 | Tetrapentyl ammonium bromide | (32.12) | 133.5 (64.96) | (2.92) |
| c | −10.6 | Trimethyl phenyl ammonium | (32.29) | 132.5 (64.77) | (2.94) |
| d | −15.4 | Dimethyl dioctadecyl ammonium bromide | (32.43) | 131.5 (64.62) | (2.95) |
| e | 1.9 | Tetraoctylammonium bromide chloride | (32.32) | 132.2 (64.74) | (2.94) |
| f | −6.6 | Hexadecyl trimethyl ammonium bromide | (32.31) | 132.3 (64.76) | (2.94) |
| g | 2.1 | Tetraethyl ammonium perchlorate | (32.29) | 132.4 (64.77) | (2.94) |
| h | −17 | Tetramethyl ammonium bromide | (31.59) | 136.9 (65.53) | (2.87) |
| i | −3 | Tetrabutyl ammonium iodide | (32.27) | 132.5 (64.79) | (2.93) |
| j | −43.4 | Tridodecyl methyl ammonium chloride | (32.78) | 135.7 (65.33) | (2.89) |
| k | −40.4 | Trioctyl methyl ammonium chloride | (32.30) | 132.6 (64.80) | (2.90) |

TABLE II

POTENTIOMETRIC RESPONSE TO HEPARIN AND COMPOSITIONS OF MEMBRANES COMPOSED OF 66 MG PVC, 132 MG PLASTICIZER AND 6 MG ALIQUAT 336

| Membrane | ΔE 0–6.9 U/ml (in 0.15M NaCl) | Plasticizer | wt % of 66 mg PVC | mg plasticizer (wt %) | wt % of 6 mg aliquat 336 |
|---|---|---|---|---|---|
| a | −30 | Dicapryl adipate | (31.9) | 134.8 (65.2) | (2.9) |
| b | −28.5 | Di-n-hexyl azelate | (31.6) | 136.6 (65.5) | (2.9) |
| c | −18.8 | Dipropylene glycol dibenzoate | (32.3) | 132.6 (64.8) | (2.9) |
| d | −5.7 | Tri-n-butyl citrate | (32.0) | 134 (65.0) | (2.9) |
| e | −29.3 | 2-Ethyl hexyl epoxytallate | (31.9) | 135 (65.2) | (2.9) |
| f | −29.5 | Di(2-ethylhexyl maleate)dioctyl maleate | (32.4) | 132 (64.7) | (2.9) |
| g | −25.5 | Tri-(n-octyl,n-decyl)trimallitate | (32.4) | 132 (64.7) | (2.9) |
| h | −26 | Methyl oleate | (32.2) | 133.2 (64.9) | (2.9) |
| i | −42.9 | Isopropyl palmitate | (31.9) | 135 (65.2) | (2.9) |
| j | −0.3 | t-Butyl phenyl diphenyl phosphate | (34.4) | 137 (65.6) | (2.9) |
| k | −28.1 | Butyl octyl phthalate | (32.4) | 131.5 (64.6) | (2.9) |
| l | −32.7 | Diisooctyl phthalate | (31.9) | 135.2 (65.3) | (2.9) |
| m | −27.6 | Glyceryl triacetyl ricinoleate | (32.3) | 132.4 (64.8) | (2.9) |
| n | −25.2 | Dibutyl sebacate | 32.1 | 133.8 (65.0) | (2.9) |
| o | −49.6 | Isopropyl isostearate | 32.2 | 133 (64.9) | (2.9) |
| p | −40.4 | Dioctyl sebacate | 32.3 | 132.6 (64.8) | (2.9) |
| q | −29.4 | Dioctyl phthalate | (32.0) | 134.2 (65.1) | (2.9) |
| r | −10.4 | Dibutyl phthalate | (32.1) | 133.9 (65.0) | (2.9) |
| s | −12.4 | o-Nitrophenyl octyl ether | (31.7) | 136 (65.4) | (2.9) |

Table II demonstrates that significant potentiometric responses can be achieved in PVC membranes plasticized with various plasticizers. Particularly outstanding responses were observed with membranes (i), (o), and (p).

EXAMPLE 3

The potentiometric response of various heparin-selective polymer membrane compositions doped with different quaternary ammonium salts are summarized in Table III below. The compositions of Table III basically comprise 66 mg PVC, ~132 mg DOS, and 6 mg quaternary ammonium salt. The weight percentages of the various components in the resulting membrane are given in parentheses on the table. The potential response is shown on the table as ΔE (mV) between an aqueous 0.15M NaCl solution and 6.9 U/ml heparin in an aqueous solution of 0.15M NaCl. Table III demonstrates that significant potentiometric responses can be achieved with various quaternary ammonium salts.

EXAMPLE 4

A heparin-selective polymer membrane electrode made in accordance with the present invention was tested in samples comprising human whole blood. The results are shown on FIG. 5 which is a graphical representation of the response characteristics of the heparin-selective electrode to specimens of undiluted human blood containing different levels of heparin. The potential in mV is plotted against time. For purposes of comparison, a 15 minute increment is marked on the chart.

The samples, designated by letters (a) to (i), were obtained as clinical specimens from one patient. A quantity of whole blood was withdrawn from the patient and divided into samples having no heparin (a) and heparin in varying added amounts (b) to (g). Then, heparin was administered to the patient and a second specimen (h) was withdrawn for a clinical assessment of heparin concentration in the blood using the heparin-selective polymer membrane electrode of the present invention. Next, protamine was administered to the patient to neutralize the heparin and a third specimen (i) was withdrawn. The sample contents are summarized as follows:
(a) whole blood, no heparin
(b) whole blood, heparin concentration of 1.00 U/ml (c) whole blood, heparin concentration of 1.58 U/ml
(d) whole blood, heparin concentration of 2.51 U/ml
(e) whole blood, heparin concentration of 3.98 U/ml
(f) whole blood, heparin concentration of 6.31 U/ml
(g) whole blood, heparin concentration of 10 U/ml
(h) whole blood, heparin concentration unknown
(i) whole blood, protamine-neutralized, remaining heparin concentration unknown Referring to FIG. 5, the electrode's response toward heparin in samples (h) and (i) is stable within less than 1 minute. Clotting-time based estimates of the actual heparin content of samples (h) and (i) correlate well with the heparin concentration determined through use of the electrode with a pre-constructed calibration curve.

Figure 5:
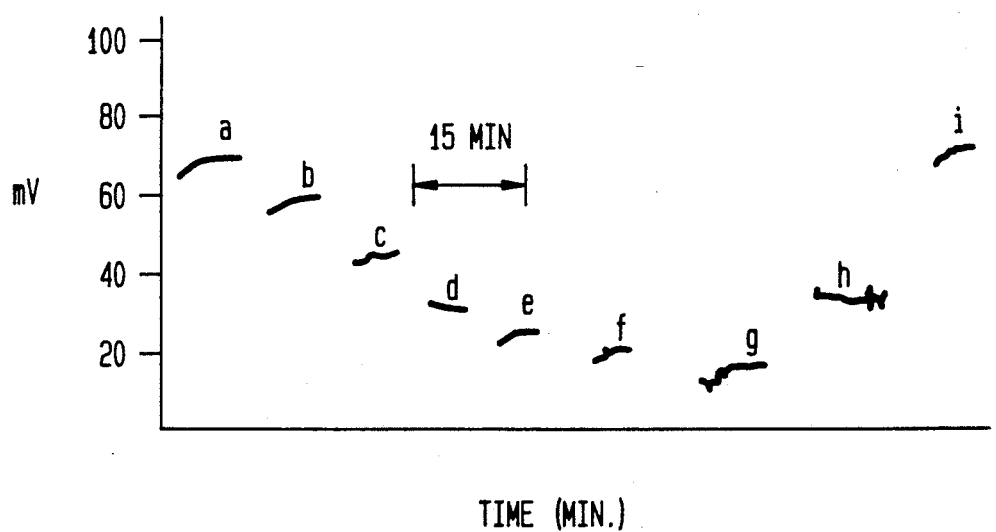
FIG. 5 is a graphical representation of the response characteristics of a heparin-selective electrode to undiluted human blood samples.

The wash-out time, or time required for the signal to return to baseline, using a 2M NaCl solution to dissociate the heparin bound to the electrode surface was less than 5 minutes in for the results recorded on FIG. 5. Shorter wash-out times are possible with higher concentration NaCl solutions.

The heparin-selective polymer membrane sensor of the present invention yields fast and reliable potentiometric response to heparin. The dynamic response time is less than 1 minute at clinically important heparin concentrations in undiluted human plasma or blood samples. The return to baseline potential time is less than 5 minutes. Thus, the heparin-selective polymer membrane sensor is suitable for use as a single-use disposable device, or as a more permanent sensor within an instrument-based system wherein the response to heparinized blood can be reversed by flushing with a high concentration salt solution between discrete sample measurements. In certain embodiments, the heparin-selective polymer membrane sensor can be adapted for continuous in vivo sensing.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. An ion-selective electrode membrane comprising, in admixture, a polymeric matrix material, an anion exchange material, and a plasticizer, the electrode membrane admixture being selective to heparin.

2. The electrode membrane of claim 1 wherein the anion exchange material is selected from the group consisting of a quaternary ammonium salts, quaternary phosphonium salts, and quaternary arsonium salts.

3. The electrode membrane of claim 2 wherein the anion exchange material is a quaternary ammonium salt.

4. The electrode membrane of claim 3 wherein the quaternary ammonium salt is selected from the group consisting of triethyl phenyl ammonium iodide, tetrapentyl ammonium bromide, trimethyl phenyl ammonium, dimethyl dioctadecyl ammonium bromide, tetraoctylammonium bromide chloride, hexadecyl trimethyl ammonium bromide, tetraethyl ammonium perchlorate, tetramethyl ammonium bromide, tetrabutyl ammonium iodide, tridodecyl methyl ammonium chloride, polybrene, and trioctyl methyl ammonium chloride.

5. The electrode membrane of claim 4 wherein the quaternary ammonium salt is tridodecyl methyl ammonium chloride.

6. The electrode membrane of claim 1 wherein the polymeric matrix material is selected from the group consisting of polyvinyl, polyurethane, cellulose triacetate, and poly(vinyl alcohol)/poly(vinylchloride) copolymer.

7. The electrode membrane of claim 6 wherein the polymeric matrix material is polyvinylchloride.

8. The electrode membrane of claim 1 wherein the plasticizer is selected from the group consisting of dicapryl adipate, di-n-hexyl azelate, dipropylene glycol dibenzoate, tri-n-butyl citrate, 2-ethyl hexyl epoxytallate, di(2-ethylhexyl maleate)dioctyl maleate, tri-(n-octyl,n-decyl)trimallitate, methyl oleate, isopropyl palmitate, t-butyl phenyl diphenyl phosphate, butyl octyl phthalate, diisooctyl phthalate, glyceryl triacetyl ricinoleate, dibutyl sebacate, isopropyl isostearate, dioctyl sebacate, dioctyl phthalate, dibutyl phthalate, and o-nitrophenyl octyl ether.

9. The electrode membrane of claim 8 wherein the plasticizer is dioctyl sebacate.

10. An electrode membrane comprising:
   30-70 weight percent polymeric matrix material;
   30-70 weight percent plasticizer; and
   0.1-12 weight percent anion exchange material, the membrane being selective for heparin.

11. The electrode membrane of claim 10 wherein the anion exchange material is a quaternary ammonium salt selected from the group consisting of triethyl phenyl ammonium iodide, tetrapentyl ammonium bromide, trimethyl phenyl ammonium, dimethyl dioctadecyl ammonium bromide, tetraoctylammonium bromide chloride, hexadecyl trimethylammonium bromide, tetraethyl ammonium perchlorate, tetramethyl ammonium bromide, tetrabutyl ammonium iodide, tridodecyl methyl ammonium chloride, polybrene, and trioctyl methyl ammonium chloride.

12. The electrode membrane of claim 11 wherein the quaternary ammonium salt is tridodecyl methyl ammonium chloride.

13. The electrode membrane of claim 10 wherein the polymeric matrix material is selected from the group consisting of polyvinyl, polyurethane, cellulose triacetate, and poly(vinyl alcohol)/poly(vinylchloride) copolymer.

14. The electrode membrane of claim 13 wherein the polymeric matrix material is polyvinyl chloride.

15. The electrode membrane of claim 10 wherein the plasticizer is selected from the group consisting of dicapryl adipate, di-n-hexyl azelate, dipropylene glycol dibenzoate, tri-n-butyl citrate, 2-ethyl hexyl epoxytallate, di(2-ethylhexyl maleate)dioctyl maleate, tri-(n-octyl,n-decyl)trimallitate, methyl oleate, isopropyl palmitate, t-butyl phenyl diphenyl phosphate, butyl octyl phthalate, diisooctyl phthalate, glyceryl triacetyl ricinoleate, dibutyl sebacate, isopropyl isostearate, dioctyl sebacate, dioctyl phthalate, dibutyl phthalate, and o-nitrophenyl octyl ether.

16. The electrode membrane of claim 15 wherein the plasticizer is dioctyl sebacate.

17. A electrode membrane having selectivity for heparin comprising:
   about 1.4 to 2.0 weight percent tridodecyl methyl ammonium chloride;
   about 65 weight percent polyvinyl chloride; and
   about 33 weight percent dioctyl sebacate.

18. An ion-selective membrane electrode comprising:
(a) a housing containing a reference solution;
(b) an electrode arranged in the housing so that it is disposed in the reference solution; and
(b) an ion-selective membrane of a polymeric matrix material which is non-reactive with the liquid medium, an anion exchange material, and a plasticizer, the ion-selective membrane being selective to heparin, the ion-selective membrane being disposed on one end of the housing so as to seal the reference solution inside the housing and to contact a sample solution external to the housing.

19. A solid state membrane electrode for measuring the concentration of heparin in a liquid medium as a function of potentiometric response comprising a conductive substrate and a membrane material arranged to be in adherence with said conductive substrate, said membrane material comprising a polymeric matrix material which is non-reactive with the liquid medium, an anion exchange material, and a plasticizer, said membrane material being selective to heparin.

* * * * *